(12) United States Patent
Reichert (10) Patent No.: US 10,117,732 B2
(45) Date of Patent: Nov. 6, 2018

(54) ARRANGEMENT HAVING AT LEAST ONE WORKPIECE FOR SINTERING

(71) Applicant: Amann Girrbach AG, Koblach (AT)

(72) Inventor: Axel Reichert, Widnau (CH)

(73) Assignee: Amann Girrbach AG, Koblach (AT)

( * ) Notice: Subject to any disclaimer, the term of this patent is extended or adjusted under 35 U.S.C. 154(b) by 0 days.

(21) Appl. No.: 14/778,648

(22) PCT Filed: Feb. 28, 2014

(86) PCT No.: PCT/AT2014/000041
§ 371 (c)(1),
(2) Date: Sep. 21, 2015

(87) PCT Pub. No.: WO2014/169304
PCT Pub. Date: Oct. 23, 2014

(65) Prior Publication Data
US 2016/0051350 A1    Feb. 25, 2016

(30) Foreign Application Priority Data

Apr. 18, 2013  (EP) .................................... 13002056

(51) Int. Cl.
*A61C 13/12*       (2006.01)
*F27B 17/02*       (2006.01)
(Continued)

(52) U.S. Cl.
CPC .......... *A61C 13/12* (2013.01); *A61C 13/0006* (2013.01); *A61C 13/20* (2013.01);
(Continued)

(58) Field of Classification Search
CPC ..... A61C 13/12; A61C 13/0006; A61C 13/20; F27D 7/06; F27B 17/025; B22F 3/1003;
(Continued)

(56) References Cited

U.S. PATENT DOCUMENTS 2,002,241 A    5/1935 Forde
3,295,844 A    1/1967 Neeley et al.
(Continued)

FOREIGN PATENT DOCUMENTS

CN    201543821    8/2010
CN    102901356    1/2013
(Continued)

OTHER PUBLICATIONS

DE 20 2010 007 606 U1 (WDT Wolz Dental Technik Gmbh) Sep. 2, 2010 (English language machine translation). [online] [retrieved on Mar. 17, 2017]. Retrieved from: Espacenet.*
(Continued)

*Primary Examiner* — Nahida Sultana
(74) *Attorney, Agent, or Firm* — Volpe and Koenig, P.C.

(57) ABSTRACT

An arrangement (1) including at least one workpiece (2) for sintering, more particularly a dental workpiece, and having at least one support material (3), and including a sintering apparatus (4) for sintering the workpiece (2), wherein the sintering apparatus (4) has at least one gas inlet duct (5) for protective gas and at least one base surface (6), and the workpiece (2) lies on the base surface (6) on the support material (3) and protrudes at least partially beyond the support material (3), wherein the protective gas can be supplied to the workpiece (2) preferably exclusively through the support material (3).

18 Claims, 5 Drawing Sheets

(51) Int. Cl.
| | |
|---|---|
| *A61C 13/00* | (2006.01) |
| *A61C 13/20* | (2006.01) |
| *B22F 3/00* | (2006.01) |
| *C04B 35/64* | (2006.01) |
| *C04B 35/111* | (2006.01) |
| *C04B 35/486* | (2006.01) |
| *C04B 35/565* | (2006.01) |
| *C04B 35/587* | (2006.01) |
| *B28B 11/24* | (2006.01) |
| *B22F 3/10* | (2006.01) |
| *F27D 7/06* | (2006.01) |

(52) U.S. Cl.
CPC ............ *B22F 3/003* (2013.01); *B22F 3/1003* (2013.01); *B28B 11/243* (2013.01); *C04B 35/111* (2013.01); *C04B 35/486* (2013.01); *C04B 35/565* (2013.01); *C04B 35/587* (2013.01); *C04B 35/64* (2013.01); *F27B 17/025* (2013.01); *F27D 7/06* (2013.01); *B22F 2003/1014* (2013.01); *B22F 2003/1042* (2013.01); *C04B 2235/658* (2013.01)

(58) Field of Classification Search
CPC .............. B22F 3/003; B22F 2003/1042; B22F 2003/1014; B28B 11/243; C04B 35/56; C04B 35/486; C04B 35/111; C04B 35/587; C04B 35/64; C04B 2235/658
See application file for complete search history.

(56) References Cited

U.S. PATENT DOCUMENTS

| | | | |
|---|---|---|---|
| 4,724,121 A | 2/1988 | Weyand | |
| 5,048,801 A | 9/1991 | Johnson et al. | |
| 5,352,395 A * | 10/1994 | Kallenbach | C04B 35/64 264/673 |
| 5,432,319 A | 7/1995 | Indig | |
| 5,604,919 A | 2/1997 | Sterzel et al. | |
| 5,911,102 A | 6/1999 | Takahashi et al. | |
| 6,027,686 A | 2/2000 | Takahashi et al. | |
| 6,696,015 B2 | 2/2004 | Tokuhara et al. | |
| 6,891,140 B2 | 5/2005 | Sato et al. | |
| 7,767,942 B2 | 8/2010 | Stephan et al. | |
| 8,591,803 B2 | 11/2013 | Wolff et al. | |
| 9,033,703 B2 | 5/2015 | Rohner et al. | |
| 2004/0042923 A1 | 3/2004 | Hirasawa et al. | |
| 2006/0006589 A1* | 1/2006 | Canova | B01D 1/18 264/661 |
| 2006/0154827 A1 | 7/2006 | Kanechika et al. | |
| 2008/0213119 A1 | 9/2008 | Wolz | |
| 2008/0220963 A1 | 9/2008 | Takahashi et al. | |
| 2008/0271599 A1* | 11/2008 | Edlinger | C22B 7/02 95/22 |
| 2009/0325116 A1 | 12/2009 | Matsuura et al. | |
| 2010/0044002 A1 | 2/2010 | Leffew | |
| 2010/0127418 A1 | 5/2010 | Davidson et al. | |
| 2010/0242814 A1 | 9/2010 | Jeney | |
| 2010/0274292 A1 | 10/2010 | Wolff et al. | |
| 2011/0171589 A1 | 7/2011 | Ha et al. | |
| 2011/0269088 A1 | 11/2011 | Rohner et al. | |
| 2012/0090411 A1* | 4/2012 | Perlinger | G01N 1/2205 73/863.12 |
| 2012/0174404 A1 | 7/2012 | Wolz | |
| 2013/0029279 A1 | 1/2013 | Jussel | |
| 2013/0149186 A1 | 6/2013 | Hachenberg et al. | |
| 2013/0241120 A1* | 9/2013 | Yamanishi | C04B 35/638 264/630 |
| 2014/0051014 A1* | 2/2014 | Steinwandel | H01M 4/8889 429/533 |
| 2014/0123892 A1 | 5/2014 | Vladimirov et al. | |
| 2014/0127637 A1* | 5/2014 | Gardin | B22F 3/003 432/201 |
| 2014/0299195 A1 | 10/2014 | Noack et al. | |
| 2014/0352634 A1* | 12/2014 | Sullivan | F22B 21/343 122/182.1 |
| 2015/0044622 A1 | 2/2015 | Yang et al. | |
| 2015/0287572 A1* | 10/2015 | Daugherty | H01J 37/3244 438/694 |
| 2015/0314131 A1* | 11/2015 | Stevenson | A61N 1/3754 174/650 |
| 2015/0335407 A1* | 11/2015 | Korten | A61C 13/0004 433/203.1 |
| 2016/0052055 A1* | 2/2016 | Reichert | B22F 3/003 419/57 |
| 2016/0184062 A1* | 6/2016 | Jussel | A61C 13/20 264/16 |
| 2016/0199906 A1* | 7/2016 | Mochizuki | B22D 18/04 164/284 |
| 2016/0214327 A1* | 7/2016 | Uckelmann | B29C 67/0007 |
| 2017/0167791 A1* | 6/2017 | He | F27D 3/0033 |
| 2017/0191758 A1* | 7/2017 | He | F27B 5/04 |

FOREIGN PATENT DOCUMENTS

| | | |
|---|---|---|
| DE | 202010007606 | 10/2010 |
| DE | 102009019041 | 11/2010 |
| DE | 202011005465 | 8/2011 |
| DE | 202011106734 | 1/2012 |
| DE | 202012004493 | 8/2012 |
| DE | 102011056211 | 2/2013 |
| DE | 102012100631 | 7/2013 |
| EP | 0094511 | 11/1983 |
| EP | 0480107 | 4/1992 |
| EP | 0524438 | 1/1993 |
| EP | 1645351 | 4/2006 |
| EP | 1885278 | 1/2009 |
| EP | 2470113 | 8/2013 |
| JP | S5194407 | 8/1976 |
| JP | S5681603 | 7/1981 |
| JP | S58141305 | 8/1983 |
| JP | S60224702 | 11/1985 |
| JP | H0525563 | 2/1993 |
| JP | H06330105 | 11/1994 |
| JP | 2002372373 | 12/2002 |
| WO | 2008021495 | 2/2008 |
| WO | 2009020378 | 2/2009 |
| WO | 2009029993 | 3/2009 |
| WO | 2011020688 | 2/2011 |
| WO | 2013053950 | 4/2013 |
| WO | 2014047664 | 4/2014 |
| WO | 2014169303 | 10/2014 |

OTHER PUBLICATIONS

Illustration "MULTIMAT2SINTER" Dentsply admitted prior art (Jan. 1, 2012).

Pages 5 to 7 of catalogue of Amann Girrbach AG "Ceramill Agrotherm/Argovent" published Oct. 2012.

* cited by examiner

Fig. 11

ARRANGEMENT HAVING AT LEAST ONE WORKPIECE FOR SINTERING

BACKGROUND

The invention relates to an arrangement with at least one workpiece to be sintered, in particular a dental workpiece, and with at least one supporting material and with a sintering apparatus for sintering the workpiece, wherein the sintering apparatus has at least one gas feed for protective gas and at least one base area, and the workpiece lies on the base area on the supporting material and protrudes at least partially beyond the supporting material. The invention also relates to a method for sintering at least one workpiece, in particular a dental workpiece, in a sintering apparatus.

For the sintering of workpieces, in particular dental workpieces, a wide variety of sintering apparatuses and also arrangements of the generic type have already been proposed in the prior art. In DE 20 2011 005 465 U1, concerning a different generic type, it is proposed for example to lower the workpieces to be sintered in an annular sintering tray completely within sintering granules, so that the sintering granules completely surround and cover the workpieces to be sintered during the sintering operation. It has been found from practical experience that, with this arrangement, the process of shrinkage of the workpiece that occurs during the sintering operation may be hindered, which leads to unwanted deformation of the workpiece. Arrangements of the generic type are disclosed for example in WO 2011/020688 A1. In this document it is proposed that a quartz tray should be filled during the operation of the sintering apparatus with inert beads, into which the article to be sintered is placed. To enter the quartz tray, that is to say the area around the workpiece to be sintered, the protective gas must flow around the quartz tray in order to enter the interior of the quartz tray from above. It has been found that, with this type of arrangement, a relatively great amount of protective gas is consumed during the sintering operation and impairments of the article to be sintered can nevertheless be caused by remnants of another gas, in particular oxygen.

In DE 10 2011 056 211, it is proposed to cover the tray in which the article to be sintered is located by means of a closure element, wherein the covered tray can be flowed through by protective gas or inert gas. However, it is not explained in detail in this document what form the covered tray should take to allow a flow to pass through it in this way.

Figure 5:
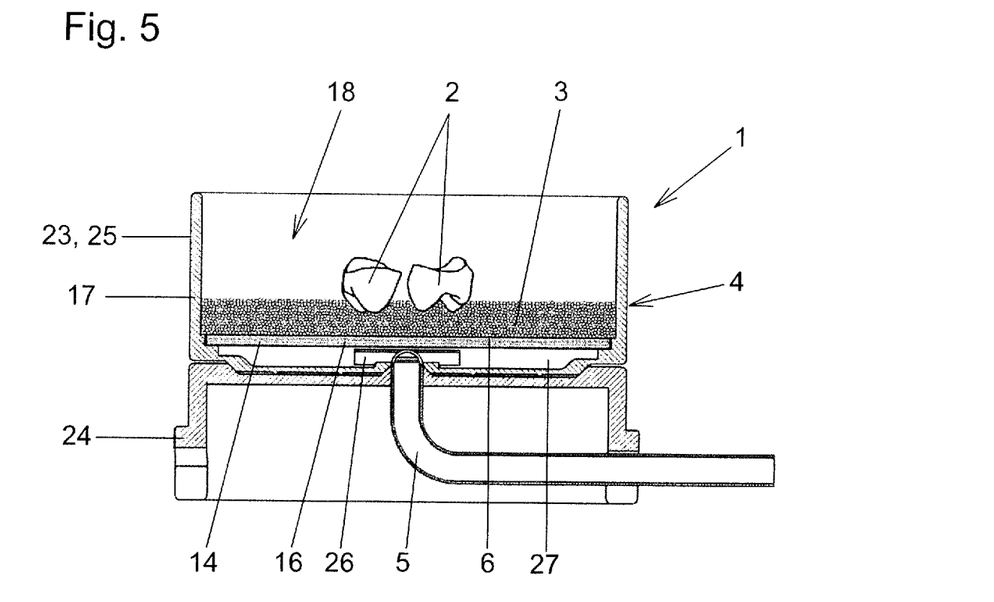

DE 10 2009 019 041 A1, concerning a different generic type, concerns a sintering apparatus for sintering magnesium or magnesium alloys at relatively low sintering temperatures of 600° C. to 642° C. under a protective gas atmosphere. In FIG. 5 of this document, it is proposed to pass any impurities of the gas in the outer region of the crucible through getter material before this impurity can get into the inner region of the crucible.

Further sintering apparatuses are shown in DE 20 2010 007 606 U1 and JP S58 141305 A. In the Japanese document it is proposed to embed the workpieces to be sintered completely in the supporting material, or to lower them in it.

Extensive tests with a wide variety of sintering apparatuses have shown that even small changes in the structure of arrangements and sintering apparatuses of the generic type can often have an unexpectedly strong influence on the quality of the sintering result, in particular at very high sintering temperatures of sometimes over 1200° C. In particular, it is difficult with arrangements known in the prior art to ensure that no undesired discoloration or oxidation of the workpiece to be sintered occurs.

SUMMARY

The object of the invention is to improve an arrangement of the generic type further to the extent that undesired adverse influences on the article to be sintered are avoided, with at the same time relatively low consumption of protective gas.

For this purpose, an arrangement according to the invention provides that the protective gas can be fed to the workpiece through the supporting material, preferably only through the supporting material.

A basic concept of the invention is consequently to ensure by structural means that the protective gas is fed to the workpiece through the supporting material, preferably only through the supporting material. As a result, the gas stream fed to the workpiece undergoes further cleaning in the supporting material in the direct vicinity of the workpiece to be sintered, whereby foreign gases that disturb the sintering operation are filtered out from the gas stream fed to the workpiece, and consequently a very clean protective gas atmosphere is achieved in the direct vicinity of the workpiece during the sintering operation. As a result of this, undesired discolorations and other impairments of the workpiece during the sintering operation can be avoided. It is ensured by the invention that the gas stream fed to the workpiece is cleaned by the supporting material directly before it reaches the region around the workpiece. As a result, a high quality of the workpieces to be produced along with relatively low protective gas consumption can be ensured even in the case of very high sintering temperatures of over 1200° C.

Gases that may be used as the protective gas are those that are already used as such in the prior art, in particular inert gases. The protective gas serves for displacing the air and other gases from the area around the workpiece and for providing a gas shroud that surrounds the article to be sintered during the sintering operation and does not react with the article to be sintered. Argon and/or nitrogen may be used for example as the protective gas.

It is favorable if the supporting material lies on the base area. Alternatively, the supporting material may however also be integrated in the base area. Since the discolorations and other impairments of the workpiece during the sintering operation are usually attributable to oxidation, particularly preferred embodiments of the invention provide that the supporting material is a material that adsorbs oxygen. The term material in this connection also includes a mixture of different materials. In other words, the supporting material consequently has at least a certain affinity, preferably a good affinity, for oxygen. It is particularly preferably provided that the supporting material has a greater affinity for oxygen than the workpiece. Affinity for oxygen is understood here as meaning the tendency of a substance or a material to adsorb oxygen, in particular by chemical reaction. The greater the affinity for oxygen of a substance or material, the more likely it is that oxygen will be adsorbed, and therefore the more oxygen will be adsorbed, on this substance or this material. Oxygen or residual oxygen in this case means the free unadsorbed oxygen, which can lead to unwanted oxidation of the workpiece. Apart from possibly present oxygen radicals, this oxygen is generally present in the air as a molecule with two oxygen atoms.

Particularly preferred embodiments of the invention provide that the supporting material comprises or is formed of granular loose material and/or at least one gas-permeable solid. In the case of granular loose material, the supporting material may consist of or comprise ceramic supporti grains, such as for example ceramic sintering beads known per se, for example of zirconium dioxide partially stabilized with yttrium. In preferred embodiments, the ceramic supporting grains have a diameter of between 0.4 mm and 2 mm. It has been found that, in the case of arrangements according to the invention, when the protective gas is passed through the supporting material a considerable cleaning effect is achieved even by using such a commonplace supporting material. In addition to the ceramic supporting grains, however, additional materials may also be added to the supporting material, for example to reduce the oxygen content. These materials or material mixtures may be formed as supporting material, but also as a gas-permeable, preferably open-pore solid. Mixed forms in which the supporting material is formed of loose material or loose material mixtures and at least one such gas-permeable solid are also possible.

The term dental workpiece comprises all those artificially fabricated components that can be used in dentures as a replacement for natural teeth or component parts of teeth, and also aids for attaching or producing such tooth replacement parts. The workpieces to be sintered are particularly preferably such workpieces of metal or metal alloys. The workpieces may be sintered in the green or white state. In arrangements according to the invention, and consequently also during the sintering operation, the workpieces lie on the supporting material, preferably directly. They therefore protrude at least partly, preferably greatly, beyond the supporting material, whereby problems with shrinkage occurring during the sintering operation are avoided.

There are various possible ways of ensuring that, according to the invention, the protective gas is fed to the workpiece through the supporting material, preferably only through the supporting material. A first group of variants according to the invention provides that the arrangement has a barrier body, which, for completely diverting the protective gas on the way to the workpiece through the supporting material, is arranged in the flow path of the protective gas between the gas feed for the protective gas and the workpiece. In the case of these variants, the barrier body consequently forces the protective gas through the supporting material before they can reach the workpiece. To achieve this, a barrier body may together with the supporting material enclose a chamber, wherein the workpiece is arranged in this chamber and the protective gas can be fed to the chamber through the supporting material, preferably only through the supporting material. The barrier body may take the form of a hollow body, wherein the hollow body has a completely closed wall apart from an opening surrounded by a periphery of the hollow body and the periphery lies completely on the supporting material or is embedded in it. Alternatively, however, it may also be provided that the barrier body takes the form of an enclosing uninterrupted wall, wherein the enclosingly uninterrupted wall has at least one opening surrounded by a periphery of the wall and the periphery lies completely on the supporting material or is embedded in it. These last-mentioned variants of a barrier body are appropriate especially whenever the protective gas has a higher density than the air to be displaced from the area around the workpiece and comprises other gases. In these embodiments, the barrier body and the supporting material can then together form a kind of tray that is upwardly open. The air and other gases are displaced from this tray by the protective gas with its higher density, so that a clean protective gas atmosphere is formed around the workpiece to be sintered by the protective gas cleaned by the supporting material.

In order that, according to the invention, the protective gas can be fed to the workpiece through the supporting material, preferably only through the supporting material, it is also possible in other embodiments, however, to dispense with corresponding barrier bodies. In particular in these variants it is provided that the protective gas coming from the gas feed can be fed to the workpiece through a through-flow region in the base area, preferably only through this through-flow region, wherein the supporting material completely covers the through-flow region or forms the full surface area of the through-flow region.

It is pointed out for the sake of completeness that this last-mentioned variant of how the protective gas is fed to the workpiece through the supporting material, preferably only through the supporting material, can also be combined with the aforementioned barrier body variants.

The through-flow region in the base area may take the form of at least one through-flow opening, preferably a number of through-flow openings, in the base area. In the case of a number of through-flow openings, a kind of screen-like construction of the base area may be obtained. It may however also be the case that the through-flow region in the base area takes the form of at least one open-pore region in the base area. The through-flow openings are usually created artificially, for example by drilling, punching, etching or the like, whereas in the case of base areas with open-pore regions a porosity with good gas permeability that already exists intrinsically in the material is used for passing the protective gas through the base area. It is of course also possible for the two variants to be combined with one another to form the through-flow region in the base area.

A base area with at least one open-pore region may be a high-temperature-resistant gas-permeable shaped body of a metallic or ceramic type. This base area may have inert properties and/or be formed as a separating layer in sheet form. Possible materials for such base areas are $ZrO_2$, $Al_2O_3$, SiC, SiN, HT alloys, etc.

Particularly preferred embodiments of the invention provide that the base area forms the bottom of a sintering tray of the sintering apparatus, wherein the workpiece is arranged in the sintering tray.

Arrangements or their sintering apparatuses according to the invention are generally used in sintering furnaces. Many of the sintering furnaces known in the prior art have a kind of flue for carrying away the gases given off during the sintering operation, which brings about a certain flue effect and consequently a perturbation of the atmosphere in the sintering furnace. In order that these flows in the sintering furnace do not cause any perturbation or turbulence of the protective gas atmosphere forming around the workpiece, preferred embodiments of the sintering arrangement according to the invention provide that the sintering chamber of the sintering apparatus is closed off upwardly by a covering. The covering may be gas-tight, but may also have at least one through-flow opening, preferably a number of through-flow openings, and/or at least one open-pore region. Open-pore regions of the covering may be formed in the same way as the open-pore regions of the base area.

The component parts of the sintering apparatus may preferably be formed of metal, metal alloys or else ceramic.

As mentioned at the beginning, apart from an arrangement according to the invention, the invention also relates to a method according to the invention for sintering a workpiece, in particular a dental workpiece. These methods are preferably carried out with an arrangement according to the invention, so that, where applicable, the statements made above concerning the embodiment according to the invention of an arrangement are also applicable to the method according to the invention described below. The method according to the invention is a method for sintering at least one workpiece, in particular a dental workpiece, in a sintering apparatus, in particular an arrangement according to the invention, wherein this sintering apparatus has at least one gas feed for protective gas and at least one base area, and the workpiece is sintered on the base area while lying on at least one supporting material and at least partially protruding beyond the supporting material, wherein the protective gas is fed to the workpiece through the supporting material, preferably only through the supporting material.

BRIEF DESCRIPTION OF THE DRAWINGS

Various arrangements according to the invention, with which methods according to the invention also can be carried out, are represented in the figures described below, in which.

DETAILED DESCRIPTION OF THE PREFERRED EMBODIMENTS

In FIGS. 1 to 6 and also 8 and 9, arrangements 1 with at least one dental workpiece 2 to be sintered and with at least one supporting material 3 and with a sintering apparatus 4 for sintering the workpiece 2 are respectively shown. The sintering apparatuses 4 have in each case at least one gas feed 5 for protective gas and at least one base area 6. Favorably, and as is the case here, the gas feed 5 is formed as a gas feed tube. In preferred variants, it could also be referred to as a gas feed line 5. The base area 6 is that area on which the workpiece can be placed during the sintering operation. The base area 6 could to this extent also be referred to as a bottom area. In all of the figures mentioned, the arrangement 1 is shown during the sintering operation. In the operating position respectively represented, the workpieces 2 to be sintered lie on the supporting material 3 and favorably protrude at least partially, preferably greatly, beyond the supporting material 3. In the embodiments, the protective gas coming from the gas feed 5 is only fed to the workpiece 2 through the supporting material 3. In the variants according to FIGS. 1 and 5, and also 8 and 9, the supporting material 3 lies on the base area 6. As still to be explained further below in detail, in the variant according to FIG. 6 the supporting material 3 is integrated in the base area 6. The supporting material 3 is favorably an oxygen-adsorbing material. The supporting material 3 may take the form of granular loose material and/or at least one gas-permeable solid or comprise such configurations.

Figure 1:
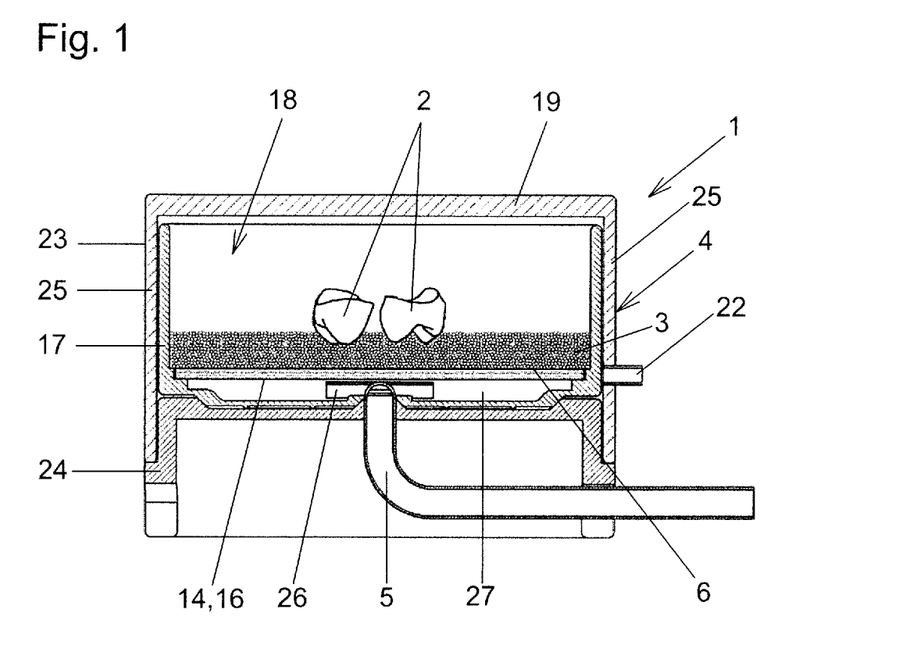
FIGS. 1 to 6 and also 8 and 9 show various embodiments of sintering arrangements according to the invention.
Figure 2:
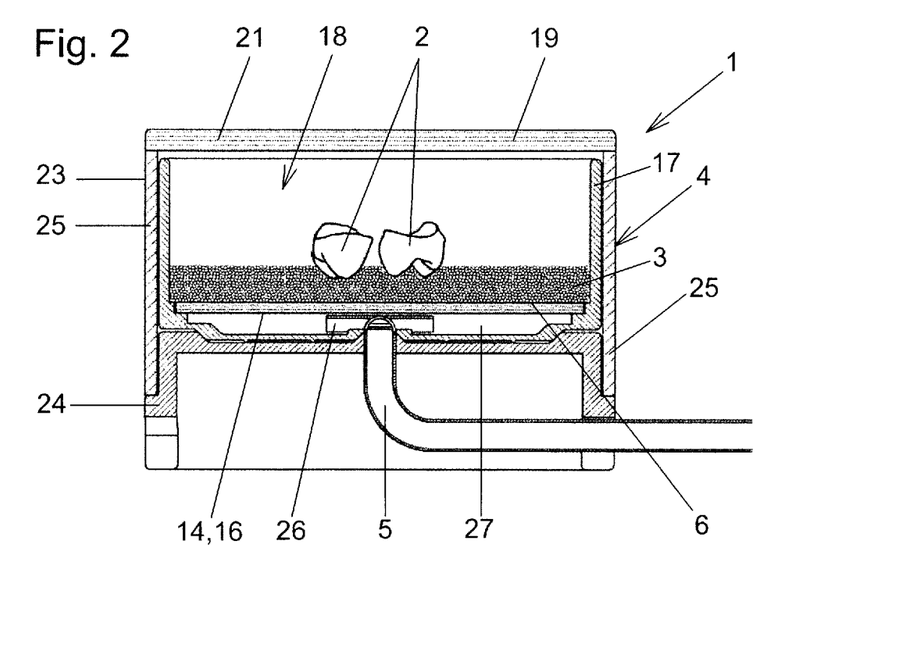
Figure 3:
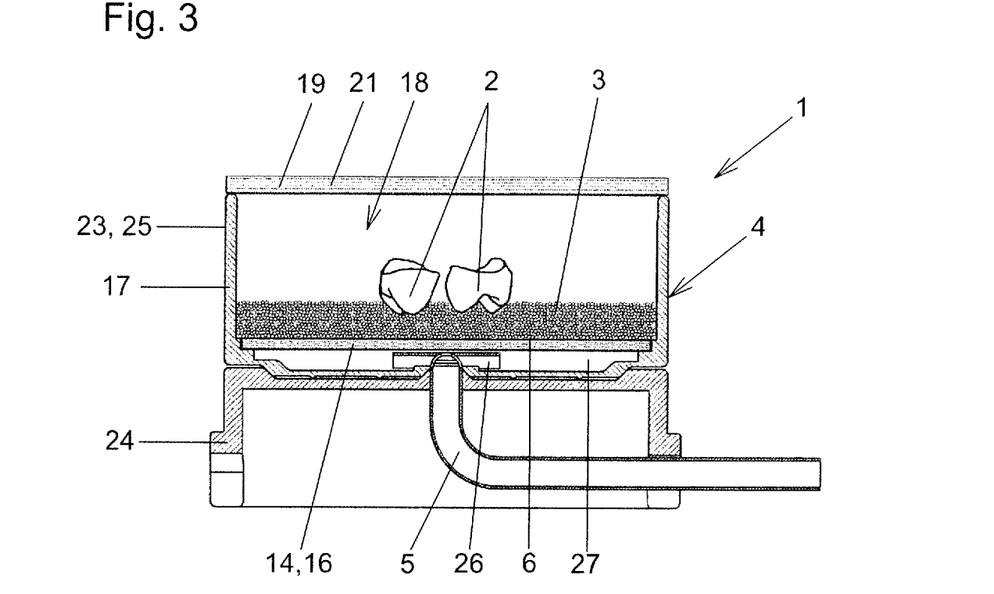

In the variants according to FIGS. 1 to 6 it is provided that the gas feed 5 is arranged on the side of the base area 6 that is facing away from the sintering chamber 18 and, for introducing the protective gas coming from the gas feed 5 into the sintering chamber 18, the base area 6 has at least one through-flow region 14 that is permeable to the protective gas. In the operating position represented, during the sintering operation, the sintering chamber 18 is delimited downwardly by the base area 6 and the gas feed 5 is arranged under the base area 6. The gas feed 5 opens out into a gas distribution cavity 27 of the sintering apparatus 4, wherein the gas distribution cavity 27 is arranged on the side of the base area 5 that is facing away from the sintering chamber 18. In the operating position represented, the gas distribution cavity 27 of these exemplary embodiments is consequently arranged under the base area 6 during the sintering operation. For the most uniform possible distribution of the protective gas flowing out from the gas feed 5, a gas distribution cap 26 may be provided in the gas distribution cavity 27, as shown in FIGS. 1 to 3 and also FIGS. 5 and 6 and as represented particularly clearly in FIG. 7.

Figure 6:
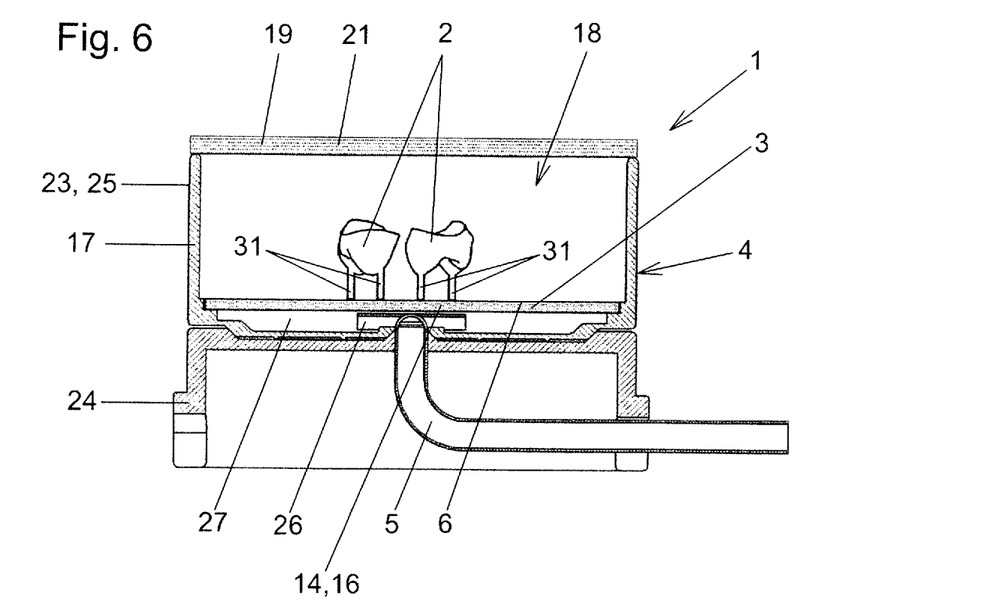

This construction also achieves the effect that the protective gas can only be fed to the workpiece 2 through the supporting material 3, in that the protective gas coming from the gas feed 5 can only be fed to the workpiece 2 through the through-flow region 14 in the base area 6, wherein the supporting material 3 completely covers the through-flow region 14, as is the case in the variants of an embodiment according to FIGS. 1 to 5, or forms the full surface area of the through-flow region 14, as is the case in FIG. 6.

The through-flow region 14 in the base area 6, through which the protective gas can enter the sintering chamber 18, may take the form of at least one through-flow opening 15, preferably a number of through-flow openings 15, in the base area 6. This is the case in the exemplary embodiment according to FIG. 4. Alternatively, the base area 6 may also have at least one open-pore region 16 or be formed in its entirety as such an open-pore region 16, as is the case in the variants of an embodiment according to FIGS. 1 to 3 and also 5 and 6. In the embodiments according to FIGS. 1 to 6 and also 8, the base area 6 forms the bottom of a sintering tray 17 of the sintering device 4 for receiving the workpiece 2 to be sintered during the sintering operation. The sintering chamber 18 lies in the interior space of the sintering tray 17. In the variants according to FIGS. 1 to 5, in each case the supporting material 3 completely covers the through-flow region 14 in the base area 6. In the variant according to FIG. 6, the supporting material 3 is integrated in the base area 6, so that the through-flow region 14 is completely formed by the supporting material 3. The sintering trays 17 of the variants of an embodiment according to FIGS. 1 to 6 and also 8 are in each case supported on a base carrier 24 of the sintering apparatus 4.

In the variant of an embodiment according to FIG. 1, the sintering tray 17 is surrounded by a hood-like outer wall 23, which is supported on the base carrier 24. This outer wall 23 of the sintering apparatus 4 comprises both the side wall 25 and the covering 19. In the exemplary embodiment according to FIG. 1, the covering 19 is of a gas-tight form. In order to allow gas to be let out from the sintering chamber 18, in this exemplary embodiment according to FIG. 1 a gas outlet 22 is provided in the outer wall 23 or the side wall 25 thereof. Both the air displaced from the sintering chamber 18 by means of protective gas and also any waste gases that may be produced at the beginning of the sintering operation, and also excess protective gas, can flow out through this gas outlet 22. The covering 19 prevents flows produced outside the sintering apparatus 4 in the sintering furnace that is not represented here from being able to disturb the protective gas atmosphere in the sintering chamber 18.

During the operation of the arrangement 1 or sintering apparatus 4 according to the invention as shown in FIG. 1, it is ensured that the protective gas is only fed to the workpiece 2 through the supporting material 3. For this purpose, the protective gas leaves the gas feed 5 and is distributed by the gas distribution cap 26 in the gas distribution cavity 27. It then passes through the through-flow region 14 of the base area 6 and is thus directed to the workpiece 2 or introduced into the sintering chamber 18, wherein it is made to pass completely through the supporting material 3, which brings about the process mentioned at the beginning of cleaning the protective gas and in particular of eliminating, or at least further reducing, the residual oxygen content. Before the actual sintering process begins, the sintering chamber 18 is flooded with protective gas, so that the air component that was previously present is displaced, preferably completely, from the sintering chamber 18. The sintering operation favorably only begins after completion of this flooding of the sintering chamber 18 with protective gas. As pointed out at the beginning, the protective gas favorably has a greater density than the air.

The sintering apparatus 4 or the arrangement 1 of the exemplary embodiment according to FIG. 2 only differs from the exemplary embodiment according to FIG. 1 by the structure of the outer wall 23. In the variant according to FIG. 2, the outer wall 23 is of a two-part construction. It has a side wall 25 in the form of the shell of a cylinder, on which a separately formed covering 19 lies. In this embodiment according to FIG. 2, the covering 19 is formed as an open-pore region 21, so that the gases emerging from the sintering chamber 18 can pass through it. This makes it possible to dispense with the gas outlet 22 in the side wall 25. In spite of its open-pore design, the covering 19 in this exemplary embodiment still ensures that no turbulences produced outside the sintering apparatus 4 can have an influence on the protective gas atmosphere in the sintering chamber 18.

It is pointed out for the sake of completeness that the open-pore regions 21 in the covering 19 and also the open-pore regions 16 in the base area 6 may be formed over the entire covering 19 or base area 6 or else only over partial regions of the respective covering 19 or base area 6.

Figure 4:
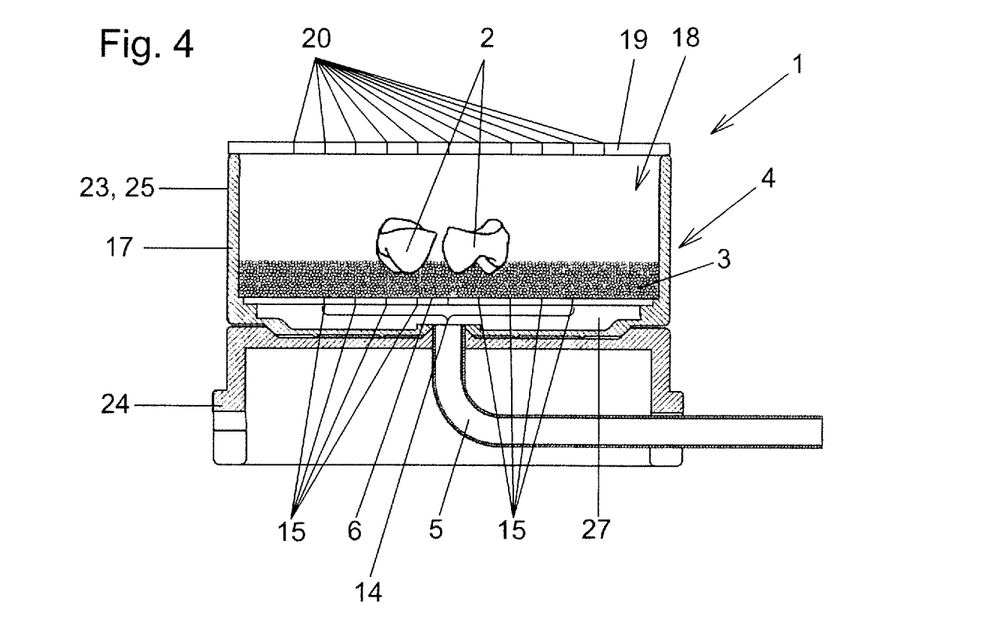

In FIG. 3 there is shown a further modified variant of a sintering apparatus 4 that dispenses with a separate side wall 25. In this variant, the outer wall of the sintering tray 17 at the same time forms the outer wall 23 of the sintering apparatus 4. The covering 19, which is likewise of an open-pore form here, lies directly on the upper periphery of the sintering tray 17. FIG. 4 shows a modification of the variant according to FIG. 3 in which the through-flow region 14 in the base area 6 is not formed as an open-pore region but as an arrangement of multiple through-flow openings 15 that are distributed over its surface area. In this variant, the covering 19 likewise has through-flow openings 20 that are distributed over its surface area. In addition, this variant dispenses with the optional gas distribution cap 26. It is pointed out for the sake of completeness that, in the case of all of the variants of an embodiment shown here, the open-pore region 16 can, where applicable, be replaced by the through-flow openings 15 in the respective base area 6 and the open-pore regions 21 can be replaced by the respective through-flow openings 20 in the covering 19, and vice versa. There may also be only a single through-flow opening 15 or 20, respectively. In all of the embodiments, it is also possible for the gas distribution cap 26 to be present or omitted.

FIG. 5 substantially corresponds to the variant according to FIG. 3, though in FIG. 5 the covering 19 has been omitted completely. This variant is appropriate especially whenever no turbulences or flows occurring outside the sintering apparatus 1 can disturb the protective gas atmosphere in the sintering chamber 18 and the protective gas has a higher density than the air to be displaced.

FIG. 6 shows further modifications of the variant according to FIG. 5, in which the supporting material 3 is formed as a gas-permeable solid and is integrated in the base area 6. Also in the case of this variant, the protective gas is only fed to the workpiece 2 through the supporting material 3. In the case of this embodiment, the workpieces 2 stand with their supporting feet 31 directly on the base area 6. In this variant, the supporting material 3 forms the through-flow region 14 over its full surface area. As an alternative to the gas-permeable solid, the supporting material 3 in this variant could also be arranged in a body similar to a mesh-like cage, the upper mesh area of which then forms the base area 6. In this variant, the supporting material 3 would then be arranged in the through-flow region 14 over its full surface area.

Figure 7:
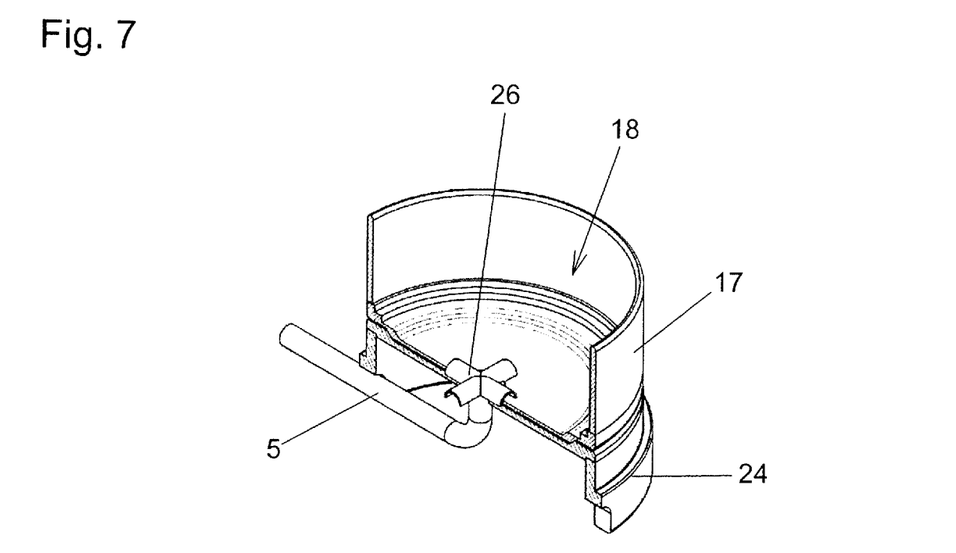
FIG. 7 shows a representation of the gas distribution cap according to FIGS. 1 to 3 and 5 and also 6.

FIG. 7 is a partially sectional representation that serves merely for illustrating a possible embodiment of the gas distribution cap 26.

Figure 8:
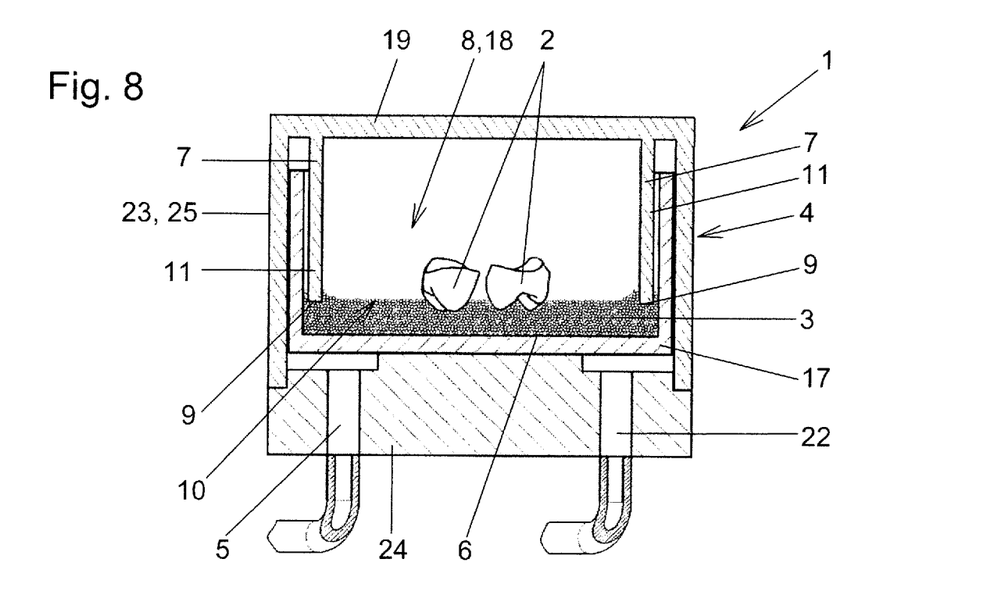
Figure 9:
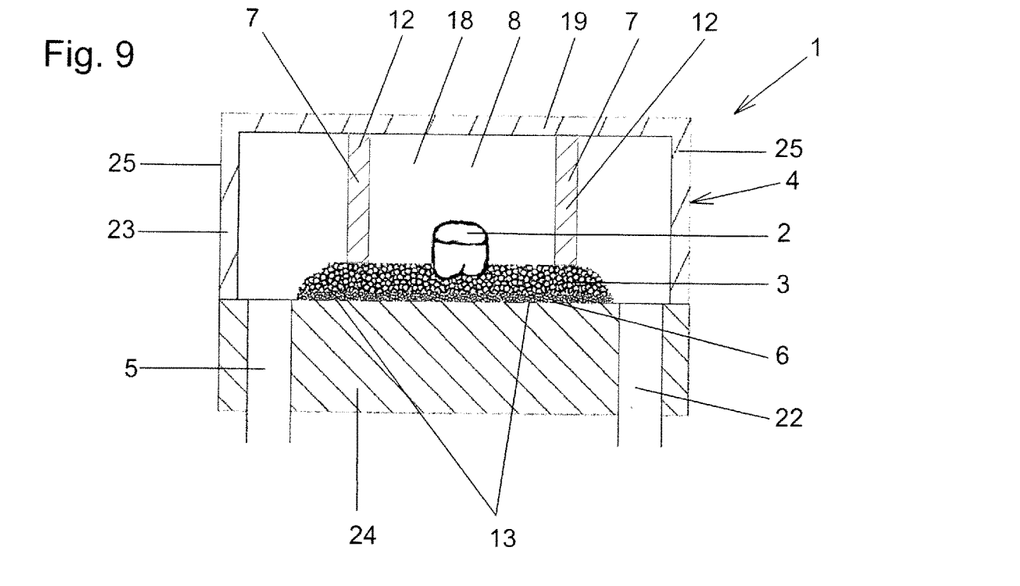

While in the case of the previously described exemplary embodiments the protective gas coming from the gas feed 5 is fed to the workpiece 2 through a through-flow region 14 in the base area 6, the variants of an embodiment according to FIGS. 8 and 9 show by way of example how the protective gas can be diverted by means of variously designed barrier bodies 7 in such a way that it can only be fed to the workpiece 2 through the supporting material 3. The barrier body 7 serves in both cases for completely diverting the protective gas on the way to the workpiece 2 through the supporting material 3 and is arranged in the flow path of the protective gas between the gas feed 5 and workpiece 2. In the first embodiment according to FIG. 8, the barrier body 7 takes the form of a hollow body, wherein this hollow body has a completely closed wall 11, apart from its opening 10 surrounding by the periphery 9 of the hollow body, and the periphery 9 lies completely on the supporting material 3 or is embedded in it. In the exemplary embodiment according to FIG. 8, the top area is integrated in the covering 19 of the outer wall 23 of the sintering apparatus 4. This does not necessarily have to be the case however; the barrier body 7 may also be upwardly closed off upwardly by a separate cover detached from the covering 19. In the variant of an embodiment according to FIG. 8, the base area 6 is the bottom of a sintering tray 17 of a gas-tight configuration. The protective gas flowing in through the gas feed 5 initially flows upward between the side wall 25 of the wall 23 and the sintering tray 17 and is then diverted by the barrier body 7 with its wall 11 into the supporting material 3, so that the entire gas stream flowing into the sintering chamber 18, and consequently to the workpieces 2, must necessarily be made to pass through the supporting material 3. In the exemplary embodiment shown according to FIG. 8, the barrier body 7 together with the supporting material 3 encloses a chamber 8, wherein the workpiece 2 is arranged in this chamber 8 and the protective gas can only be fed to the chamber 8 through the supporting material 3. In this exemplary embodiment, the chamber 8 corresponds to the sintering chamber 18. The gas or gas mixture displaced from the sintering chamber 18 leaves the sintering apparatus 4 by way of the gas outlet 22.

In FIG. 9 there is shown a second exemplary embodiment of an arrangement 1 according to the invention, or of a corresponding sintering apparatus 4, in which a barrier body 7 is used for passing the entire gas feed stream completely through the supporting material 3 before the gas can enter the sintering chamber 18, and consequently the area surrounding the workpiece 2. In the exemplary embodiment according to FIG. 9, the barrier body is an enclosing uninterrupted wall 12, which has an opening enclosed by a periphery 13 of the wall 12, wherein the periphery 13 in turn lies completely on the supporting material 3 or is embedded in it. In the exemplary embodiment shown, the upper periphery of the barrier body 7 that is facing away from the supporting material 3 lies against the covering 19 of the outer wall 23, so that the sintering chamber 18 is also closed off upwardly in the sense of stabilizing the flow as well as possible. Variants in which the upper periphery of the barrier body 7 does not reach as far as the covering 19 are also conceivable. These variants can be used if the protective gas that is used has in turn a greater density than the gases to be displaced from the sintering chamber 18, and stabilizing of the flow by covering the sintering chamber 18 is not absolutely necessary.

A further difference in the case of FIG. 9 from the embodiments shown up to now is that the base area 6, on which the workpiece 2 rests with the supporting material 3 placed in between, is not part of a sintering tray 17. The exemplary embodiment according to FIG. 9 shows by way of example that a sintering tray 17 does not necessarily have to be present. In the variant according to FIG. 9, the base area 6 is formed directly by the base carrier 24, which may also be the case in other exemplary embodiments.

Even if in the case of all the exemplary embodiments shown here the protective gas can only be fed to the workpiece 2 through the supporting material 3, this does not necessarily always have to be the case. Pathways for the protective gas to the workpiece 2 where not the entire protective gas, but preferably at least a large part of the protective gas, is made to pass through the supporting material 3 may possibly also be tolerated. This can be achieved for example in the case of the embodiments of a variant according to FIGS. 1 to 5 when not the entire through-flow region 14 is covered with supporting material. In the variants according to FIGS. 8 and 9, this would be the case for example whenever the walls 11 or 12 do not reach completely up to or into the supporting material 3 everywhere. It is preferably provided, however, that the entire protective gas is made to pass only through the supporting material 3 before it reaches the workpiece 2.

Figure 10:
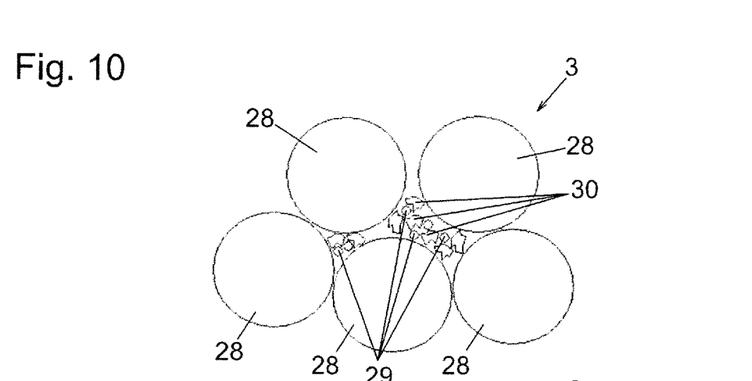
FIGS. 10 and 11 show various variants of the supporting material.
Figure 11:
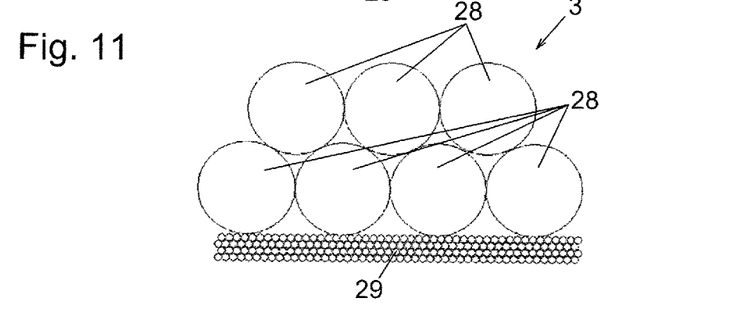

As already explained at the beginning, the supporting material 3 may for example be granules, a powder or a granule-powder mixture. The supporting material 3 may however also take the form of a gas-permeable solid or comprise such a solid. Mixed forms thereof are also possible. The supporting material 3 may for example be customary, commercially available sintering beads as they are known, for example of zirconium dioxide partially stabilized with yttrium. It has been found that such a supporting material 3 also already has a certain cleaning function and especially has an oxygen-binding function. Other ceramic supporting grains or mixtures thereof may well also be used as supporting material 3. In order to improve the cleaning function, and in particular the binding of residual oxygen, it is also possible however to mix with these ceramic supporting grains 28 an additional material 29, which may in particular have a greater affinity for oxygen than the ceramic supporting bodies 28 themselves. The greater affinity for oxygen of the additional material 29 may be achieved for example by the additional material that is used being a material or material mixture which comprises at least one chemical element or at least one chemical compound that has a greater affinity for oxygen than the material of the workpiece 2 or than the material of the ceramic supporting grains 28. In particular, the additional material 29 may serve the purpose of chemically binding the residual oxygen to it. If the additional material 29 comprises components that could become attached to the workpiece 2 during the sintering operation, it is favorable if an intermediate layer of ceramic supporting grains 28 is present between the additional material 29 and the workpiece 2. The various components of the supporting material 3 may consequently be in the form of a homogeneous or else a homogeneous mixture. Additional materials 29 with great affinity for oxygen may for example be metals or metal alloys. However, ceramic additional materials also come into consideration. The additional material 29 may likewise be in the form of pellets or powder. The additional material may for example be cobalt, chromium, molybdenum, titanium or titanium alloys. The supporting material 3 may consequently be for example a loose material consisting of two components, such as for example the ceramic supporting grain 28 and the additional material 29. However, multi-component mixtures are also conceivable. For example, a third component may be present in the supporting material 3 in the form of a carrier substance 30. This carrier substance 30 may serve the purpose that the additional material 29 is adsorbed on it. It may for example be ceramic materials such as aluminum-corundum. The carrier substance 30 favorably has a rough and/or abrasive surface. The grain diameter of the ceramic supporting grains 28 is favorably greater than the grain diameter of the carrier substance 30. The grain diameter of the additional materials 29 is then in turn favorably smaller than that of the carrier substance 30. Even when the carrier substance is absent, the grain diameter of the supporting grains is favorably greater than that of the additional material. FIG. 10 shows a supporting material 3 in the form of such a three-component mixture. The smaller grain diameter allows the carrier substance 30 together with the additional material 29 adsorbed on it to slide through between the ceramic supporting bodies 28 and be deposited at least substantially in the lower region of the supporting material 30. This has the effect, as already mentioned above, of achieving an embodiment in which at least some of the ceramic supporting bodies 28 are arranged between the workpiece 2 and the remaining component parts of the supporting material 3. FIG. 11 shows a further variant of the supporting material 3. This is a mixture of granular loose material in the form of the ceramic supporting grains 28 and a gas-permeable solid arranged thereunder, consisting of the additional material 29, which in this exemplary embodiment may in turn have a greater affinity for oxygen than the ceramic supporting grains 28 as a result of the aforementioned measures. It should be pointed out for the sake of completeness that gas-permeable solids may also be used exclusively as the supporting material 3.

| Legend for the Reference Signs | |
|---|---|
| 1 | arrangement |
| 2 | workpiece |
| 3 | supporting material |
| 4 | sintering apparatus |
| 5 | gas feed |
| 6 | base area |
| 7 | barrier body |
| 8 | chamber |
| 9 | periphery |
| 10 | opening |
| 11 | wall |
| 12 | wall |
| 13 | periphery |
| 14 | through-flow region |
| 15 | through-flow opening |
| 16 | open-pore region |
| 17 | sintering tray |
| 18 | sintering chamber |
| 19 | covering |
| 20 | through-flow opening |

| Legend for the Reference Signs | |
|---|---|
| 21 | open-pore region |
| 22 | gas outlet |
| 23 | outer wall |
| 24 | base carrier |
| 25 | side wall |
| 26 | gas distribution cap |
| 27 | gas distribution cavity |
| 28 | ceramic supporting grain |
| 29 | additional material |
| 30 | carrier substance |
| 31 | supporting foot |

The invention claimed is:

1. An arrangement comprising a workpiece to be sintered, at least one supporting material, and a sintering apparatus, the sintering apparatus includes at least one gas feed for protective gas and a base area, and the workpiece lies on the supporting material, which is integrated in or located on the base area, and protrudes at least partially beyond the supporting material, the at least one gas feed having an outlet that discharges into the supporting material such that the protective gas is fed to the workpiece only through the supporting material.

2. The arrangement as claimed in claim 1, wherein the supporting material is a material that adsorbs oxygen.

3. The arrangement as claimed in claim 1, wherein the supporting material has a greater affinity for oxygen than the workpiece.

4. The arrangement as claimed in claim 1, wherein the supporting material comprises at least one of a granular loose material or at least one gas-permeable solid body.

5. The arrangement as claimed in claim 1, further comprising a barrier body, which, for completely diverting the protective gas on the way to the workpiece through the supporting material, is arranged in a flow path of the protective gas between the at least one gas feed for the protective gas and the workpiece.

6. The arrangement as claimed in claim 1, further comprising a barrier body, which together with the supporting material encloses a chamber, the workpiece is arranged in said chamber and the protective gas is fed to the chamber through the supporting material.

7. The arrangement as claimed in claim 6, wherein the barrier body comprises a hollow body having a completely closed wall apart from an opening surrounded by a periphery of the hollow body and the periphery lies completely on the supporting material or is embedded in the supporting material.

8. The arrangement as claimed in claim 6, wherein the barrier body comprises an enclosing uninterrupted wall having at least one opening surrounded by a periphery of the wall and the periphery lies completely on the supporting material or is embedded in the supporting material.

9. The arrangement as claimed in claim 1, wherein the protective gas coming from the at least one gas feed is fed to the workpiece through a through-flow region in the base area, and the supporting material completely covers the through-flow region or is arranged in the through-flow region over a full surface area thereof or forms an entire surface area of the through-flow region.

10. The arrangement as claimed in claim 9, wherein the through-flow region in the base area comprises at least one through-flow opening or at least one open-pore region, or a combination thereof.

11. The arrangement as claimed in claim 1, wherein the base area forms the bottom of a sintering tray of the sintering apparatus, and the workpiece is arranged in the sintering tray.

12. The arrangement as claimed in claim 1, wherein the sintering apparatus has a sintering chamber in which the workpiece is arranged, and the sintering chamber is closed off upwardly by a covering.

13. The arrangement as claimed in claim 12, wherein the covering is gas-tight or has at least one through-flow opening or at least one open-pore region, or a combination thereof.

14. A method for sintering a workpiece in a sintering apparatus, comprising:
   providing at least one supporting material;
   providing a sintering apparatus including at least one gas feed for protective gas and a base area;
   placing the workpiece on the at least one supporting material, which is integrated in or located on the base area, with the workpiece protruding at least partially beyond the at least one supporting material,
   feeding the protective gas through an outlet of the at least one gas feed that discharges into the at least one supporting material such that the protective gas is fed to the workpiece only through the at least one supporting material;
   sintering the workpiece on the base area while the workpiece lies on the at least one supporting material, with the workpiece at least partially protruding beyond the at least one supporting material, and feeding the protetive gas to the workpiece through the supporting material during sintering.

15. The arrangement as claimed in claim 6, wherein the protective gas is fed to the chamber entirely through the supporting material.

16. The arrangement as claimed in claim 1, wherein the workpiece is a dental workpiece.

17. The method of claim 14, wherein the workpiece is a dental workpiece.

18. The method of claim 14, wherein the protective gas is fed entirely through the supporting material to the workpiece.

* * * * *